(12) United States Patent
Lindal et al.

(10) Patent No.: US 11,135,166 B2
(45) Date of Patent: *Oct. 5, 2021

(54) FOAM-FORMING COMPOSITIONS FOR DELIVERING AN ACTIVE TO A BODY CAVITY

(71) Applicants: Ake Richard Lindal, Malmo (SE); David Ben Ibrahim Sagna, Flyinge (SE)

(72) Inventors: Ake Richard Lindal, Malmo (SE); David Ben Ibrahim Sagna, Flyinge (SE)

(73) Assignee: PHARMIVA AB, Lund (SE)

(*) Notice: Subject to any disclaimer, the term of this patent is extended or adjusted under 35 U.S.C. 154(b) by 0 days.

This patent is subject to a terminal disclaimer.

(21) Appl. No.: 15/985,751

(22) Filed: May 22, 2018

(65) Prior Publication Data

US 2018/0338916 A1 Nov. 29, 2018

Related U.S. Application Data

(60) Provisional application No. 62/509,932, filed on May 23, 2017.

(51) Int. Cl.
*A61K 9/12* (2006.01)
*A61K 33/40* (2006.01)
(Continued)

(52) U.S. Cl.
CPC .............. *A61K 9/124* (2013.01); *A61K 9/006* (2013.01); *A61K 9/0014* (2013.01);
(Continued)

(58) Field of Classification Search
CPC ...... A61K 33/40; A61K 9/122; A61K 9/0041; A61K 47/06; A61K 9/124; A61K 45/06;
(Continued)

(56) References Cited

U.S. PATENT DOCUMENTS

| 4,684,479 A | 8/1987 | D'Arrigo |
| 5,554,315 A | 9/1996 | Tonomura |

(Continued)

FOREIGN PATENT DOCUMENTS

| EP | 0250539 | 1/1988 |
| EP | 1121089 | 4/2000 |

(Continued)

OTHER PUBLICATIONS

Attassi F., Servin, A., "Individual and co-operative roles of lactic acid and hydrogen peroxide . . . " FEMS Microbiological letter 394 (2010) 29-38.

(Continued)

*Primary Examiner* — Kyung S Chang
(74) *Attorney, Agent, or Firm* — Jeffrey S. Melcher; Melcher Patent Law PLLC (57) ABSTRACT

Provided is a foam-forming formulation and method of administrating a medically active or cosmetic or reliving compound to the skin, to a would or to a body cavity. The foam-forming formulation contains monoglyceride crystals, a hydrophilic blowing agent in an amount to blow the foam-forming composition and form a foam, water, and a medical, cosmetic or reliving compound. The foam-forming composition is suitable application to skin, wounds and body cavities when blown to form the foam and the foam melts at a body temperature to release the content. Also provided is a foam-forming composition vehicle for delivering an active agent.

28 Claims, 1 Drawing Sheet

(51) Int. Cl.
| | |
|---|---|
| A61K 9/00 | (2006.01) |
| A61K 47/06 | (2006.01) |
| A61K 45/06 | (2006.01) |
| A61K 47/12 | (2006.01) |
| A61K 47/02 | (2006.01) |
| A61K 47/14 | (2017.01) |
| A61K 47/24 | (2006.01) |
| A61P 17/10 | (2006.01) |
| A61P 17/06 | (2006.01) |
| A61P 13/10 | (2006.01) |
| A61K 47/18 | (2017.01) |
| A61P 15/00 | (2006.01) |
| A61P 29/00 | (2006.01) |

(52) U.S. Cl.
CPC .......... *A61K 9/0031* (2013.01); *A61K 9/0034* (2013.01); *A61K 9/0041* (2013.01); *A61K 9/0043* (2013.01); *A61K 9/122* (2013.01); *A61K 33/40* (2013.01); *A61K 45/06* (2013.01); *A61K 47/02* (2013.01); *A61K 47/06* (2013.01); *A61K 47/12* (2013.01); *A61K 47/14* (2013.01); *A61K 47/18* (2013.01); *A61K 47/24* (2013.01); *A61P 13/10* (2018.01); *A61P 15/00* (2018.01); *A61P 17/06* (2018.01); *A61P 17/10* (2018.01); *A61P 29/00* (2018.01)

(58) Field of Classification Search
CPC ........ A61K 47/12; A61K 47/02; A61K 47/14; A61K 47/18; A61K 47/24; A61K 9/00; A61P 17/10; A61P 17/06; A61P 13/10
See application file for complete search history.

(56) References Cited

U.S. PATENT DOCUMENTS

| | | | |
|---|---|---|---|
| 5,576,016 | A | 11/1996 | Amselem |
| 5,693,258 | A | 12/1997 | Tnomura |
| 6,156,294 | A | 12/2000 | Mautone |
| 6,589,518 | B2 | 7/2003 | Steer |
| 7,141,237 | B2 | 11/2006 | Abram |
| 7,374,747 | B2 | 5/2008 | Abram |
| 7,709,026 | B2 | 5/2010 | Bologna |
| 7,749,488 | B2 | 7/2010 | Abram |
| 8,193,244 | B1 | 6/2012 | Stockel |
| 8,476,319 | B2 | 7/2013 | Scholz |
| 8,512,723 | B2 | 8/2013 | Scholz |
| 8,586,008 | B2 | 11/2013 | Abram |
| 2005/0255052 | A1 | 11/2005 | Adams |
| 2007/0292355 | A1 | 12/2007 | Tamarkin |
| 2007/0299043 | A1 | 12/2007 | Hunter |
| 2008/0299520 | A1 | 12/2008 | Ali |
| 2011/0189637 | A1 | 8/2011 | Anderson |
| 2016/0081968 | A1* | 3/2016 | Svensson ............... A61K 33/38 424/616 |
| 2016/0201186 | A1 | 7/2016 | Durham |

FOREIGN PATENT DOCUMENTS

| | | |
|---|---|---|
| WO | 2006/131784 | 12/2006 |
| WO | 2008/075207 | 6/2008 |
| WO | 2011/039637 | 4/2011 |
| WO | 2016/048230 | 3/2016 |

OTHER PUBLICATIONS

Arzhavitina A, Steckel H. "Foams for pharmaceutical and cosmetic application". Int J Pharm. Jul. 15, 2010;394(1-2):1-17. doi: 10.1016/j.ijpharm.2010.04.028. Epub Apr. 29, 2010.
Written Opinion issued in corresponding international application No. PCT/SE2015/051011, dated Dec. 1, 2016, pp. 1-7.
International Search Report issued in corresponding international application No. PCT/SE2015/051011, dated Dec. 1, 2016, pp. 1-6.
Krog, "Phase behavior and rheological properties of aqueous systems of industrial distilled monglycerides," Chem. Phys. Lipids 2 (1968) pp. 129-143.
Remington: The science and practice of Pharmacy edited by David B. Troy, Paul Beringer, Chapter 50 p. 1000 by John J Sciarra and Christopher J Sciarra, 21st edition, 2006, copyrights to the University of the Sciences, Philadelphia.
UNC Eshelman school of Pharmacy, Campbell University.
Response filed in corresponding European Patent Application No. 18729059.8-1109, dated May 12, 2021, pp. 1-14.
Office Action issued in corresponding European Patent Application No. 18729059.8-1109, dated Nov. 10, 2020, pp. 1-9.
Tang Christina et al: "Responsive foams for nanoparticle delivery", Colloids and Surfaces. B, Biointerfaces, Elsevier, Amsterdam, NL, vol. 133, May 27, 2015 (May 27, 2015), pp. 81-87.
Office Action issued in Indian counterpart application IN 201947047096, Office action (OA1) dated Jul. 25, 2020, pp. 1-6.
Response filed in Indian counterpart application IN 201947047096, dated Mar. 24, 2020, pp. 1-8.
Response to Form 18 filed in ARIPO Patent Application No. AP/P/2019/012072, dated Jun. 16, 2021, pp. 1-9.
Hearing Notice issued in POC/Application No/201947047096, dated Jul. 8, 2021, pp. 1-2.
Form 18 issued in ARIPO Patent Application No. AP/P/2019/012072, dated Jun. 24, 2021, pp. 1-5.
Article 94 communication in European Patent Application No. 18 729 059.8-1109, dated Jun. 18, 2021, pp. 1-5.

* cited by examiner

FOAM-FORMING COMPOSITIONS FOR DELIVERING AN ACTIVE TO A BODY CAVITY

FIELD OF THE INVENTION

The invention relates to foam-forming compositions containing crystalline lipids and methods for local delivery of medically active agents to skin or a body cavity. The invention also relates to a novel foam delivery system and method of delivery.

BACKGROUND OF THE INVENTION

We have found that topical and intracavital foam formulations are suitable for the delivery of medically active agents. A foam has several attractive properties in medical treatment since it has a capacity to spread over large surfaces and it has low density which makes administration to sensitive areas, such as wounds, infected or inflamed areas or post-surgery tissue of the skin less painful. Foam also spreads well in body cavities.

Monoglycerides have been used with lipid propellants. If however a lipid propellant is used in combination with crystalline monoglycerides we have found that the resulting product is inhomgenous and not crystalline. We have surprisingly found that if polar or hydrophilic propellants are used we can maintain the crystalline structure of the monoglycerides and the resulting product is stable and homogenous.

There are several problems associated with the delivery of drugs to a body cavity and to skin. One important issue is the distribution of the drug. Semisolid formulations, creams, gels and ointments are not able to generate uniform drug delivery to the body cavity area. Furthermore administration of semisolids to sensitive areas of the skin is less suited since the mechanical work to administer the product may create pain and discomfort. Foam formulations based on lipid crystalline formulations may be the solution for this problem. The treatment of infections and inflammations in the reproductive organs such as STI, sexually transmitted infections, bacterial vaginosis and vulvovaginitis is one area where the invented foam has advantages with respect to drug distribution and delivery. Also the treatment of vaginal discomfort such as malodour, pain, itch and increased vaginal fluid excretion are problematic. The overuse of systemic treatment with active agents, such as antibiotics, has led to development of resistance and the diversity of the diseases, which leads to the need for several treatments with different actives that increase the risk for maltreatment. The difficulty of diagnosing is another issue that can make therapies inefficient. Local treatment has so far been inefficient. The reasons for the inefficacy of local treatment is partly lack of effective local agents but also ineffective surface cover of the local product. A gel product or a vagitorium does not deliver drug to the entire area in the reproductive organs.

Local treatment of diseases in body cavities such as vagina, urethra, ear, anus and the nasal cavity in general require treatment of the entire area in the body cavity. If only a part of the area is treated local infections and inflammations may remain partly untreated and will soon recover its original streght. Intra-cavital preparations such as gels, ointments, vagitories/suppositories and tablets have the draw back that only a minor part of the surface is treated. In the case of systemic delivery of active compounds by administration in body cavities the lack of surface coverage means that only a small and from time to time varying area is exposed. This will lead to an unpredictable drug uptake and to a variation in the biological response and medical effect, and risk for resistance development. In contrast, the present novel delivery system is capable of treating the entire surface of a body cavity due to its solid crystalline structure in a composition selected to provide a mechanically stable foam. The body cavities may be natural or artificial body cavities, created by wounds or surgery.

Another aspect of of topical drug delivery where a foam is needed is administration to large and sensitive areas. The treatment of sensitive areas, as in dermatitis and in infected or chronic wounds, will benefit from a minimum of physical contact and here the use of the invented foam is beneficial for the patient and patient compliance.

The usefulness of using foams for the treatment of body cavities is described in Arzhavitina A, Steckel H. "Foams for pharmaceutical and cosmetic application". Int J Pharm. 2010 Jul. 15; 394(1-2):1-17. doi: 10.1016/j.ijpharm.2010.04.028. Epub 2010 Apr. 29. Foam containing monoacylglycerides are not common. In U.S. Pat. No. 4,684,479 the use of acylmonoglycerides in foams, formation of microbubbles, is described. There is no information on the melting point and the acylmonoglyceride is not in crystalline form. In U.S. Pat. No. 5,554,315 the use of acylmonoglycerides to improve physical properties of foams based on surfactants, polyoxyalkylene ethers are described. In U.S. Pat. No. 5,693,258 the use of acylmonoglyceride polyoxyethylene derivatives for foams is described. The use of acylmonoglycerides alone or their crystals is not mentioned. In U.S. Pat. Noss. 7,141,237 and 7,374,747 the use of higher alcohols, C14 to C22, a small alcohol C1 to C6 water and a surfactant for the generation of a temperature sensitive foam is described. In the presentations of the invention no acylmonoglyceride is mentioned and the formulations contain a surfactant based on an ester of laurinmonoglyceride. In U.S. Pat. No. 7,749,488, a foam consisting of ethanol, water, a surfactant, a pH adjusting compound and a propellant is described in the first claim. The surfactant is defined as a compound from the groups of block-co-polymers, fatty acid and/or fatty alcohol etoxylates, polysorbates and glycerol ester etoxylates. A person skilled in the art may add one or several of the surfactants of these groups to the invented composition for the purpose of improving physical properties, but the present invention is based on the use of crystalline lipids and their melting at temperatures below 37° C., which is not disclosed in this patent. In U.S. Pat. No. 8,193,244 the use of C12 monoacylglycerol in combination with long chain dibasic amino acid alkyl ester salts has been claimed as a synergistic antimicrobial combination, which is not relevant for a foam application. The use of C12 acylmonoglcyeride for the treatment of otitis has been described in U.S. Pat. No. 8,476,319 but there is no teaching of the use of the acylmonoglyceride in crystalline form nor its melting.

In U.S. Pat. No. 8,512,723 the use of C12 acylmonoglyceride is described. However, in this patent the product must contain at least 50% of hydrophobic compound and there is no teaching of the use of the acylmonoglyceride in crystalline form and/or its melting. In U.S. Pat. No. 8,586,008 a foam for topical purposes containing various medical agents is presented. The patent teaches that the melting point of this foam can be regulated with the presence of ethanol. In the invented formulation the melting temperature is regulated by the mixing proportions of acylmonoglycerides. The presence of ethanol increases solubility of the acylmonoglycerides, thereby inhibiting the formation of crystals that is important for the properties of the foam. The patent teaches away from using crystals in the formulation.

In (Tamarkin) WO2011039637 the main claim in this patent application is "A substantially surfactant free foamable composition comprising: a) about 60% to about 95% by weight of a hydrophobic solvent, or about 1% to about 80%) by weight petrolatum and about 15% to about 94% by weight hydrophobic solvent, wherein if combined the total amount of hydrophobic solvent and petrolatum is at least about 60%> by weight". This patent application does not teach the use of crystalline lipids in a water base to form a foam.

My previous application, published as U.S. serial No. 2016-0201186 on 14 Jul. 2016, is incorporated herein by reference.

There is a need for improvements in treating infections in body cavities, in wounds and on skin, especially under conditions where classical antibiotics may not be effective and/or where there is a risk for resistance development. There is a need for a product that can be administered immediately upon the discovery of an infection without any risk of creating antibiotic resistance to the infecting agent and with a high probability of efficient treatment irrespective of the nature the infecting agent, e.g. bacteria, virus, fungi and flagellates.

Another issue is the physical stability of the formulation during storage. If lipophilic propellants are used the monoglycerides will undesirably dissolve in the propellants. This will reduce the amount crystalline monoglycerides and phase separation will occur. In fact the formulation will be in the form of a two phase system containing a lipid phase consisting of a solution of monoglycerides in the by pressure solidified propellants and a water phase containing water, crystalline monoglycerides with a hydrophilic surface and other hydrophilic elements. When release from the compressed state the propellant will evaporate and leave a semisolid film of water and a mixture of crystalline and amorphous lipids. Nonlimiting examples of such unsuitable lipid propellants are propane, butane and isopropane. When such unsuitable propellants are used the stability of the foam is impaired and the foam forming capacity is compromised. A suitable propellant should be able to maintain the crystalline structure of the monoglycerides both in the container during shelf life and after having produced a foam. Examples of suitable propellants are polar and hydrophilic ones that as the main part contain air or gaseous mixture simulating air, oxygen, nitrogen, carbon dioxide. In the present invention we demonstrated that the use of air and similar propellants are superior the use of lipid propellants. Another aspect of using air as propellant or foam forming agent is the possibility to form foams at low pressures or at ambient pressures. This property was discovered when formulations containing air were stored. Microscope investigation revealed stable air bubbles over time. This feature can be used to distribute foam products in non pressurized containers which is a large advantage from industrial and safety point of view.

Suitable medically active agents are agents that are effective in the treatment of skin infections and inflammation, in the treatment of conditions in wounds and in body cavities. Non-limiting examples of medically active agents are anti-inflammatory agents, antibiotics, antivirals, antifungals, anti-psoriatic agents, agents for the control of humidity or pH in skin as well as agents for the treatment of acne.

Another issue in treating skin, open wounds or cavities of the body is the use of foreign matter. Lipid propellants exemplified by propane or butane are not physiological and such compounds are not suitable for human or animal use in body cavities.

SUMMARY OF THE INVENTION

The present invention solves the problems mentioned herein above by providing a dense and stable foam. The product is mixed with or pressurized by nonlipophillic gases to generate stable lipid crystals. The product is adapted for use on skin, in wounds or other skin areas with impaired protective function and in body cavities.

The present invention comprises a suspension or a semi-solid preparation containing crystalline monoglycerides, mixed with a propellant (blowing agent) to form foam. The mixing can be done under pressure, up to 10 bar, or during ambient conditions 1 bar. By administering the product in the form of foam, the entire volume of the cavity or the entiry surface of the area can be filled. The foam is constructed to physically decompose, melt, at a skin temperature and thereby the entire surface of the cavity will be treated.

The present invention also relates to a novel foam-forming delivery system comprising solid crystals of lipids that decomposes (melts) at body temperature. The foam is strong and stable at sub decomposition (melting) temperatures thus being able to cover even the narrowest parts of the internal volume of body cavities or area to be treated on skin. Once the volume or area is covered by the foam, the foam is heated by the body or skin until the foam reaches a decomposition temperature and the crystals melt and the foam breaks due to the elevated temperature. The melted remains of the decomposed foam, a nonrunny viscous fluid, coat the tissues of the treated area. Such foam is useful for delivery of medically active agents to the skin and the interior of body cavities. The product can also be used for systemic delivery via body cavities or the skin.

The lipid crystal has a solid form that is sufficient to maintain a foam structure at a temperature below the body and skin temperatures (98.6° F. or 37° C. and 93.2° F. or 34° C.). The foam can be manufactured by two modes. One is during the manufacturing process by mixing polar gases into the product and the product is then stored in the form of a foam at normal pressure. The other way is to introduce a blowing gas into the formulation and to store the product at elevated pressure, up to 10 bar, in a pressurized can. The foam forming composition comprising lipid crystals and at least one active is stored, and a propellant can used to blow the foam-forming composition and form the foam during application to a cavity or to skin. Once the foam is in place, the foam is heated by the body. When the foam reaches a decomposition temperature (the decomposition temperature is less than or equal to the body/skin temperature), the lipid crystals melt and the foam breaks down releasing the trapped blowing gas and active agent from the foam to form a layer of active agent on exposed tissue within the cavity or the treated area.

The present invention further relates to a method of administering locally or systemically active agents to tissues on the skin or within body cavities. As earlier described, there are several problems associated with dermal and intracavital drug administration. A solution to these problems is to deliver the medically active agent in the form of a foam of crystalline lipids that melt at body temperature. The foam has a structure, below the melting temperature, strong enough to allow the foam to be distributed into an entire volume of a cavity while at the same being able to adhere to the entire surface once melted. The foam is also strong enough to allow administration to skin without immediately breaking down.

The present invention further relates to the foam forming composition, disclosed herein, in combination with a delivery device capable of generating a foam of the composition and comprising a foam guiding conduit adapted to provide delivery of the foam into a body cavity or a skin area. The conduit is generally adapted to enable administration initially to the parts of the body cavity furthest away from the entrance, e.g. having adequate length, and thereafter to the outer parts e.g. while withdrawing the conduit in a controlled and predetermined manner.

Objectives of the invention can be obtained by a foam-forming composition adapted for treating a disease on skin or in a body cavity comprising:
monoglyceride crystals in an amount to form a foam;
a nonlipophillic blowing agent in an amount to blow the foam-forming composition and form a foam;
at least one medical agent effective against diseases of the skin or body cavity; and
water, wherein the foam-forming composition is configured for application to body cavity when blown or mixed to form the foam and the form degrades at a body temperature to release the medically active agent. All % are by weight of the total composition unless otherwise stated.

Objectives of the inventions can also be obtained by a foam-forming pharmaceutical composition for delivering an active agent to a body cavity comprising:
water;
solid lipid crystals suspended in the water, the solid lipid crystals having a melting point in their crystalline state of less than 37° C. and more than 25° C.; and
a propellant for blowing the composition and forming a foam, wherein the solid lipid crystals being present in an amount to support a foam when the composition is blown by the propellant, and the composition is adapted for application to the body cavity when blown so that when the foam is heated by the body cavity the foam degrades at the melting point and releases contents of the foam to tissues in the body cavity.

Objectives of the invention can also be obtained by adapting the composition of the foam such that upon melting it contacts the surface of the cavity to deliver the active principle and the contacting form is resistant to removal by flow of wound or vaginal fluids.

Objectives of the inventions are preferably obtained by guiding the delivery of the foam formed from the foam-forming compositions to a body cavity with a foam guiding conduit adapted to provide delivery to the entire body cavity.

DETAILED DESCRIPTION OF THE INVENTION

Foam Formulations.

The present invention can be a form that forms a foam when mixed with a blowing gas. This can be performed by adding the blowing gas during manufacture at normal pressure (1 bar) while mixing and by packing the gas mixed product at normal pressure or by adding a blowing gas under pressure, up to 10 bar, and storing it in a pressurized container where the foam is mainly generated at the application of the product to skin or body cavities. The formulation is advantageously a suspension of lipid crystals and can be mixed or pressurized with a blowing gas to form a foam. In the present formulation we have found that a preferable combination of two monoglycerides, C12 monolaurine and C14 monomyristine can create a foam that will decompose when exposed to temperatures at skin or body temperature. This embodiment will describe the preferred use of this foam. However, the formulation can utilize any foam that will decompose when exposed to human body temperatures, including the novel foam delivery system described herein, and convention foams. Thus, any suitable foam forming composition can be used, and the invention is not limited to the preferred examples disclosed herein.

In order to exercise a medical effect the formulation must be in physical contact with the affected tissue. Local formulations in the form of fluids and semisolids are only in contact with a minor part of the mucosal tissue and are thus not able to exercise its full effect. In the present formulation the foam first fills the entire cavity or skin area and secondly the foam decomposes due to the melting of the monoglycerides by the body temperature. This way the entire inner surface of the treated area is covered and treated with the formulation when the foam decomposes and releases the active agent to the entire affected area.

A foam can be generated by addition of a propellant (blowing agent) suitable for human use, exemplified but not limited to air and carbondioxide. Any desired, suitable blowing agent can be used in an amount sufficient to provide the foam during application to the body cavity. An exemplary amount of propellant is amounts that induces a pressure from atmospheric pressure to 10 bar. The amount of propellant can depend on the desired structure of the foam as evaluated by a skilled artisan.

Furthermore, the present invention can contain an additional stabilizer in the form of crystalline lipids such as monoglycerides in the amount of 1 to 35%. The monoglycerides are 1-Glycerolmonolaurate, C12, and 1-Glycerolmonomyristate, C14. The amount of and the ratio between C12 and C14 can be varied depending on the required viscosity of the final product. The ratio C12 to C14 can vary from 1 to 3 to 1 to 1 for a cream product and 1 to 3 to 1 to 0 for a lotion/spray form product with lower viscosity. The amount of lipids in a cream can vary between 15 and 35% while lotions and sprays has a preferable lipid content of 1 to 15%. The monoglycerides are in crystalline form in the final formulation. The manufacture of the monoglyceride crystalline dispersion is performed by heating all components, see examples, to 70° C. and cool at a fixed rate, 0.5 to 5° C. per minute, until crystallisation starts at 30 to 39° C. Before or during the crystallization process gas can be mixed into the product by stirring of by the use of homogenizers. The gas will remain in the product during the rest of the production process and during packaging. Such products are not pressurized but a storage stable foam is formed.

In one embodiment of the novel foam delivery system, we have invented a formulation that in the presence of a propellant (blowing agent), such as a non-lipophilic gas, is able to form foams comprising (solid) lipid crystals. Such crystals may comprise single lipids or a mixture of lipids. Suitable lipids are phospholipids, mono and di acylglycerides. N-acetylethanolamides and esters of lactic acid and fatty acids. Since the lipids are in their crystalline state, the foam will maintain its structure while filling the body cavity. The lipids should be at least partly in their crystalline state, more preferable to 50% and even more preferable to 70% and most preferably to 80% determined by scanning calorimetry.

Crystalline lipids are defined by a continuous repeated structure in three dimensions but the nature of the repetition may not be the same in all directions. The crystals may contain bilayers of water and lipid creating a repeated structure of water and lipid layers in one direction and lipid crystals in two directions. An easy way to detect crystallinity is to study birefringence in microscope. For example, a definition of a lipid lamellar crystal is a solid crystal with three dimensional continuity having the same repeated cells in two dimensions, but a different one in the third dimension, from Small, The lipid handbook, which can be established by wide angle X-ray ref. The crystallinity of monoglycerides in the compositions can be determined by differential scanning calorimetry, DSC. The transfer from solid liquid crystals is exothermic and gives rise to a release of energy. This can be determined by a scanning calorimeter.

There are several advantages associated with the use of (solid) lipid crystals. Since the crystalline state in general is the lowest energetic state very little will happen with the structure during storage. In contrast to emulsions and liquid crystals which are changing over time by crystallization, sedimentation or coalescence, the solid lipid crystalline structures does not change over time in a pharmaceutical perspective. Stable constituents are regarded as a large advantage in the development of pharmaceutical products.

Another embodiment of the invention is the ability of the foam to decompose (melt) at skin temperature or in the body cavity. When lipid crystals melt the gas will be released and the foam will decompose to form a solution that can coat the tissue on skin or in the body cavity. The content of the foam, active agents, pH modifying agents, etc. will be released to the tissue and the product can exert its effect. Such foam should preferably melt at a temperature of 25 to 37° C. more preferable at 30 to 37° C. and most preferably at 32 to 37° C.

Yet another embodiment of the invention is the ability to fill the internal volume of a body cavity and to cover a surface once melted to enable medically active agents to be in the formulation to make good contact with the mucosal membrane at the site of administration.

The foam delivery formulations according to the present invention can comprise a solvent or dispersion media, preferably water. The water can make up the balance of the composition. The solid lipid crystals are present in an amount suitable for forming the foam, for example from 0.5 and 30%. The composition can also include pH and tonicity regulating compounds and pharmaceutically active agents. The formulations can also contain agents for improving foam properties and non-limiting examples are nonionic surfactants of high HLB. Examples of such surfactants are esters of fatty acids and alcohols or saccharides of polar nature.

In a typical but non-limiting procedure the solid lipid crystals are manufactured by heating the lipid(s) in water to 70 to 75° C. to melt the lipids followed by cooling to room temperature to solidify the lamellar crystals. The medically active agent can be added prior to, during or after heating and even after cooling. The cooled dispersion of crystals can then be diluted, if required, and mixed with other agents prior to packing in a pressurized container. Non-limiting examples of such agents are pH modifiers, solvents, viscosity enhancers, chemical and physical stabilizers, humectants, emollients and preservatives.

In a further embodiment of the invention, the product can be presented in a pressurized container containing a suitable propellant (blowing agent). Non-limiting examples of suitable propellants in contact with the product are air or similar compositions of oxygen and nitrogen, nitrogen, oxygen and carbon dioxide. Other suitable propellants are hydrophilic ditto and mixtures of these. By hydrophilic we mean that the propellant cannot dissolve the crystal structure of the monoglycerides at storage temperatures between 0 and 30 C. The amount of propellant required is the amount sufficient to form a suitable foam. This is individual and depending on the composition and the desired properties of the foam and this can be evaluated by a person skilled in the art.

Figure 1:
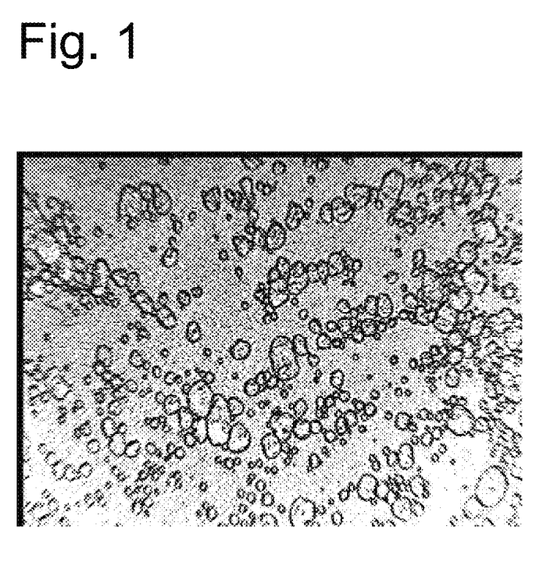
FIG. 1 is a picture of a foam formed according to Example 16.
Figure 2:
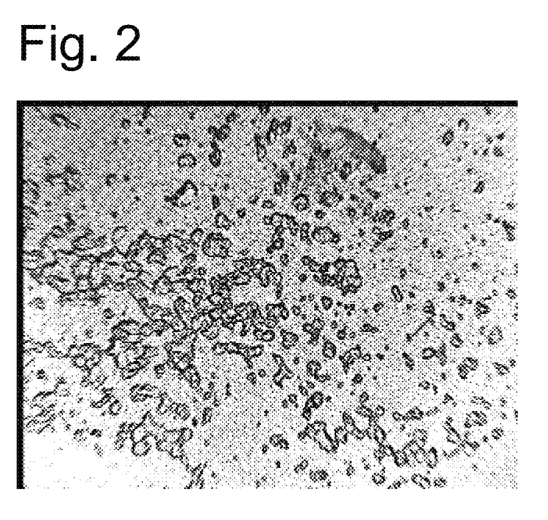
FIG. 2 is a picture of the foam of FIG. 1 after 1 month of storage.

In further embodiments, the foam delivery system can be presented in the form pressurized packaging. This can be of an open interior where all of the propellant is mixed with the product or in the form of a bag on valve container where the product is contained in a small polymeric/sandwich membrane bag inside the container and thus separated from the bulk of the propellant, as shown in FIGS. 1 and 2. Different propellants can be used inside and outside this bag to optimize foam properties and product stability. Propellants that are not in contact with the composition during storage can be the earlier mentioned hydrophilic ones or any suitable lipophiillic propellant such as butan, propan etc, including mixtures with the earlier mentioned hydrophilic ones.

In preferred embodiments the foam delivery system presented in a pressurized container, packaging, or the like, comprises a foam guiding conduit adapted to provide adequate delivery to all areas of the body cavity to be treated. Based upon the teachings of the present disclosures selection of conduit can be made by one skilled in the art.

In yet another preferred embodiment of the invention the product is mixed with the blowing gas at ambient pressure. Such product can be stored in nonpressurized containers exemplified but not limited to pumps intended for storage and delivery of detergents and soaps.

Generally a foam guiding conduit is adapted when applying to a body cavity to result in a coverage of the inner cavity surface greater than that achievable in the absence of the conduit, advantageously complete coverage. In alternative embodiments the coverage can be selected from more than any of: 50%, 60%, 70%, 80% and 90%.

Any desired active agent utilized for treating and/or preventing a condition, disease, infection, or other, in a body cavity can be used in the present invention in their pharmaceutically effective amounts.

In another embodiment the foam can be used for the treatment of local diseases such as infections by bacteria, fungi, virus, parasites or other microorganisms. Non-limiting examples of such infections are bacteria or fungal vaginosis and sexually transmitted infections such as, gonorrhea, syphilis and chlamydia. Other examples are otitis and nasal infections as well as prophylactic treatment against infection or inflammation after surgery. Another example is prophylaxtic use of the product in order to avoid fungal infections caused by shaving (*tinea barbae*) involving Dermatophytes or *Malassezia folliculitis*.

Other medical indications suitable for treatment by this invented product are local inflammatory processes exemplified but not limited to vulvovaginitis. Suitable compounds are steroids and nonsteroidal anti-inflammatory agents.

Other examples of suitable medical indication are psoriasis and useful medical agents that can be incorporated in the foam formulation are vitamin D3 antagonists and steroids. Compounds useful in the treatment of eczema can also benefit from the introduction into the invented foam formulation. Examples of such compounds are steroids, NSAIDs and COX 2 inhibitors.

Yet other medical indications are preparations for the treatment of ulcers or reduction of scar formation after ulcers generated by surgery or by other causes. Non-limiting examples of suitable compounds are collected from the group of growth factors or compounds having effect on release of growth factors.

Fungal infections on skin or wounds or in body cavities can be treated using the invented foam including an antifungal agent effective against dermatophytes or *candida* species.

Another medical condition that can be treated with the invented formulation is urinary incontinence. Non-limiting examples of suitable substances are anticholineric compounds such as Oxybutynin, Tolterodine, Darifenacin, Solifenacin, Trospium, Fesoterodine, and bladder relaxing compounds such as Myrbetriq.

The administration of foam to body cavities can be used to treat a systemic disease. Application of a foam to a body cavity can create a large application area and favorable conditions for penetration though or into mucus membranes.

In yet other embodiments of the invention we have found that surface active agents may be useful in the composition. These agents can improve foam properties but also increase the contact between waxy surfaces such as in the ear, and the product.

The invention also relates to methods of treating a condition in a body cavity comprising forming a foam from the foam-forming composition comprising HP, hydrogen peroxide, monoglyceride crystals in an amount to form a foam, at least one acid and/or buffer which is present in an amount to provide a pH of 3 to 5 within a body cavity and water by blowing the foam with a blowing agent in an amount to blow the foam-forming composition and form the foam. The methods include applying the foam to a body cavity to coat tissues in the body cavity with the foam-forming composition with the blowing agent and/or allowing the body to heat the foam to a decomposition temperature of the foam, wherein the foam degrades and releases the hydrogen peroxide to the tissues in the body cavity at a pH of 3 to 5, and/or guiding the foam by a foam guiding conduit.

The invention also relates to a method of delivering an active agent to tissues in a body cavity comprising forming a foam from a foam-forming pharmaceutical composition for delivering an active to a body cavity comprising water, an active agent, and solid lipid crystals suspended in the water, the solid lipid crystals having a melting point in their crystalline state of less than 37° C. and more than 25° C. by blowing the foam-forming composition with a blowing agent. Applying the foam to a body cavity to coat tissues in the body cavity with the foam-forming composition with the blowing agent. Allowing the body to heat the foam to a decomposition temperature of the foam, wherein the foam degrades and releases the active agent to the tissues in the body cavity, and/or guiding the foam by a foam guiding conduit.

Effects of Hydrogen Peroxide.

One problem in the treatment of sexually transmitted and other vaginal infections, exemplified but not limited to, gonorrhea and bacterial vaginosis is the development of resistance towards antibiotics. The antibiotics are specific in their action and operate on the bacteria cell membrane and small alterations in the cell wall synthesis can lead to inactivation of the antibiotic. Antiseptics with less specific action such as peroxides, halogens such as chlorine and iodine, phenols and alcohols, as well as phenolic and nitrogen compounds are less likely to generate resistance due to their general bactericidal effect. However, the lower specificity leads in general to larger risk for toxicity. Of the listed antiseptics most of them are unsuitable for administration into body cavities. One that is suitable is hydrogen peroxide (HP).

It is known that peroxides and in particular HP is an effective antiseptic compound and that most microorganisms are sensitive to HP. We have found that the present invention is capable of eradicating the relevant bacteria when present in a pharmaceutically effective amount. Preferred amounts of HP include from 0.05 to 1%, more preferable 0.05 to 0.7% and most preferable 0.1 to 0.6%. In this application, the content of an ingredient is given in % by weight based on the total weight of the composition.

HP has been administered to humans for over 100 years and one problem that has limited the use of HP has been the auto-oxidation of hydrogen peroxide. This phenomenon leads to a rapid degradation of HP as soon as HP is exposed to reactive matter. The fast reaction leads to boiling, development of oxygen a degradation product of HP, and the HP is consumed within minutes or seconds. With the presence of crystalline acyl monoglycerides, preferably from C12 to C14, the rate of degradation of HP at the site of action can be regulated and optimized for maximum effect. This procedure has been described in the literature for use on skin at higher concentrations of HP. This procedure has however not been demonstrated for use in body cavities, and neither for low amounts of HP, such as 0.5% and below.

HP can be enzymatically degraded, e.g. by catalases and there are at least two sources of catalase in vaginal and urethral infections and that is the naturally occurring catalase from eukaryote cells and the other is the catalase generated by the pathogens, i.e. *N. gonorrhoea* and *G. vaginalis*. The catalase is effective at a pH over 5 and in order to avoid this effect the product advantageously contain an alpha hydroxyl acid in an amount sufficient to keep the pH in the body cavity between 3 and 5, preferably between 3.5 and 4.5. Any acid or buffer system suitable for application to a body cavity can be utilized. In the case of the vagina, a preferred acid is lactic acid since lactic acid is already present in the vagina. Other preferred acidifying agents are polymers and oligomers of lactic acid, glycolic acid and acrylic acids or combinations thereof.

The amount of alpha hydroxyl acid in the composition, combinations of monomers and/or oligomers and/or polymers present is preferably 1 to 10%, more preferably 2 to 7%, and most preferably 3 to 6%. In order to operate inside a smaller pH range some of the acid may be replaced by with the salt of the acid or with bases to make a buffer. The final pH should preferably be between 3 and 6, more preferably between 3.5 and 5 and most preferably between 3.5 and 4.5 when exposed to 1 to 10 parts of vaginal fluid.

A nonlimiting example of a alpha hydroxyl acid is Lactic Acid.

Another important property of the present invention is the ability to regulate pH at the application site. The pH in a healthy vagina is about 4 while the main site of gonorrhea infections for men, the urinary tube, is between 8 and 5 with good opportunities for catalase activity. The present invention contains alpha hydroxyl acids with the purpose of keeping the intra-vaginal pH sufficiently low to inhibit the catalases. Preferably, the amount of acid is sufficient to provide a pH below 5 in order to inhibit catalase activity generated by the pathogens or by invading cells, local or from plasma. In order to provide a pH between 3 and 5 the use of at least one buffer based on alpha hydroxyl acids are preferred. A preferred buffer is lactic acid buffer. Preferred pHs are from pH 3 to 5 and more preferably a pH of 3.5 to 4.5. The buffer is preferably present in an amount to be able to keep the pH below 5 when diluted in vaginal or urethral fluids.

Treatment of skin diseases require may a low pH, between 5 and 5.5, to avoid local irritation. Any physiologically acceptable buffer system can be used for this purpose and a skilled artisan can evaluate the amount of buffer needed.

Stabilizers for Hydrogen Peroxide

The present invention contains at least one, preferably at least two, and more preferably several stabilizers for HP in order to avoid auto-oxidation. Stabilizers for HP are well-known and any suitable stabilizer can be utilized.

A polycarboxylic acid having a chain length of 2 to 6 carbon atoms, preferably oxalic acid has shown stabilizing effects on HP. The acids can be added to the formulation as salts or as the acid. A most preferred acid of this type is oxalic acid. The acids are preferably added in concentrations between 0.05 and 0.5% and more preferably 0.1 to 0.3%.

Tin, in the form of a salt, either as sodium salt or as a pyrophosphate can be present in an amount of 0.005 to 0.05% or preferably 0.01 to 0.03% corresponding to the amount of tin.

Salicylic acid can be added in an amount of 0.02 to 0.5%, preferably 0.05 to 0.2%. Salicylic acid can also be added as a salt of salicylic acid. Concentrations of Salicylic acid above 0.5% are preferably avoided since above this level pharmacological effects of Salicylic acid could be expected.

The present invention can be adjusted to a pH with respect to the stability of HP. In this stabilizer combination, the preferred pH during storage was found to be 3.5 to 4.5, which was unexpected in view of the prior art teachings e.g. those of Schumb et al and other authors referred to in the background section. If not buffered the pH in the present invention typically increases after manufacture, e.g. a formulation that immediately after manufacture has a pH of 4.5 will typically increase to pH 5 after a few weeks storage and remain below pH 5.3 for the remaining shelf life period.

Additional stabilisers such as pyrophosphate and sequestrants, such as but not limited to EDTA and phosphonic acids as well as salicylic acid, are also possible to incorporate into the formulation. Physical stabilisers, against sedimentation of the lipids, such as polar surfactants with HLB over 20 and thickeners such as polyacrylic acid derivatives can also be added to the formulation to improve its properties. Traditional dermatological agents such as glycerol and propyleneglycol can be added.

Other active principles may have other requirements on stabilizers. The use of vitamin or derivatives thereof, gallates or other known stabilizers are possible to include in the invented formulations.

EXAMPLES

Some of the products manufactured as examples has been subject to microscope investigation to evaluate foam forming and foam stability. The has been done in light microscope, Motic B3 professional, using a magnification of 4×10. The airbubbles found were all irregular, no spheres, in shape indicating that the structure forming the airbubbles are in solid state and not liquid.

Example 1

The formulations in table 1 were manufactured and tested for content of HP by a permanganate titration method, USP, assay for HP. The manufacture was performed according to the following procedure. EDTA, sodium stannate, sodium pyrophosphate, and sodium oxalate were dissolved in water. If applicable, thickening agents are included at this point. Lactic acid and sodium hydroxide were added and pH adjusted. The monoglycerides were added and the mixture was heated to 70 to 75 C and kept there for 15 minutes while stirring. After 15 minutes slow cooling, less than 5 C per minute, was applied to about 35 when crystallisation occurred followed by an increase in temperature. After the crystallisation was completed hydrogen peroxide was added. The products were packed in spray containers consisting of a metal can and a laminate internal bag. The product was premixed with air and filled inside the bag on valve and additional air up to a pressure of 5 bars. The product was stored at 30° C., 25° C. and 3 to 8° C. Analysis of the content of HP was made by a titration method including dissolution of the compositions in acetic acid and titration to color shift by potassium permanganate.

TABLE 1

Formulations for stability testing (% w/w).

| | A | D | E | F |
|---|---|---|---|---|
| EDTA | 0.05 | 0.05 | 0.05 | 0.05 |
| Sodium pyrophosphate | 0.025 | 0.025 | 0.025 | 0.025 |
| Sodium stannate | 0.04 | 0.04 | 0.04 | 0.04 |
| Sodium oxalate | 0.14 | 0.14 | 0.14 | 0.14 |
| Lactic acid (90%) | 5.00 | 5.00 | 5.00 | 5.00 |
| Glycerol monolaurate | 0.625 | 2.5 | 2.5 | 5.0 |
| Glycerol monomyristate | 1.875 | 7.5 | 7.5 | 15.0 |
| H2O2 | 0.3 | 0.3 | 0.1 | 0.5 |
| 10M NaOH | 3.00 | 3.00 | 3.00 | 3.00 |
| HPLC water | To 100 | To 100 | To 100 | To 100 |
| pH | 3.5 | 3.5 | 3.5 | 3.5 |
| Stability* | | | | |
| Initial | 3.20 | 3.31 | 1.24 | 5.29 |
| 30 C. 30 days | 2.74 | 2.77 | 0.87 | 4.56 |

*Remaining amount of hydrogen peroxide (mg/g)

Example 2, Foam Forming

We have studied the effect of the amount of lipids on the ability to form a foam and the stability of HP. The formulations were manufactured according to example 1 and aerosols were produced by, under pressure, adding 0.25% of air or a mixture 50/50 of pharmaceutical grade propane and butane into an aerosol container having an inner container of a polymer protecting the product against the metal material in the container.

TABLE 2

Foaming versus amount of monoglycerides(%)

| Ingredient | 1 | 2 | 3 | 4 |
|---|---|---|---|---|
| 1-glyceryl-monolaurate | 2.5 | 2.5 | 5 | 1.25 |
| 1-glyceryl-monomyristate | 7.5 | 7.5 | 15 | 3.75 |
| Myrj 59 | 0.1 | 0.1 | 0.1 | 0.1 |
| Lactic acid | 3.0 | 3.0 | 3.0 | 3.0 |
| Sodium hydroxide | 0 | 0 | 0 | 0 |
| Purified water to | 100 | 100 | 100 | 100 |
| pH | 4 | 4 | 4 | 4 |
| Butane/propane | 8 | | | |
| Air to pressure (atm)* | | 5.5 | 5.5 | 5.5 |

*Corresponds to about 0.25 g of air.

All three batches that contain air produced a white solid foam when released from the can, which was observed by the naked eye. The foam produced by the batch that contained butane/propane produced an inhomogeneous off whit/yellow foam. The product was tested for crystallinity of monoglycerides using a DSC, differential scanning calorimeter. The products that contain air show a level of crystallinity of more than 70%. The container that was pressurized by butane demonstrated a level of crystallinity of less than 50%.

Example 3

Effect of propellant on hydrogen peroxide stability Manufacture: EDTA and the sodium salts were dissolved in a major part, 75%, of the water. Lactic acid and sodium hydroxide were added and pH adjusted. The monoglycerides were added and the mixture was heated to 70 to 75 C and kept there for 15 minutes while stirring. After 15 minutes slow cooling, less than 5 C per minute, was applied to about 35 C when crystallisation occurred followed by an increase in temperature. After the crystallisation was completed a hydrogen peroxide and the remaining water was added. The products were packed in spray containers consisting of a metal can and a aluminium/polymer laminate internal bag. The same propellant was used in and outside the laminate bag. When filing butane and propane mixtures a weight is filled but when air is used as propellant it is filled up to a determined pressure. The reason is that propane and butane are fluids at a pressure of 3 to 6 atm depending on the mixture while air turns into a fluid at about −190 C.

TABLE 3

| | Compositions | | |
|---|---|---|---|
| Ingredients | 3:1 | 3:2 | 3.3 |
| Monolaurine | 2.5 | 4.5 | 4.5 |
| Monomyristine | 7.5 | 13.5 | 13.5 |
| EDTA | 0.05 | 0.05 | 0.05 |
| Sodium pyrophosphate | 0.025 | 0.025 | 0.025 |
| Sodium stannate | 0.04 | 0.04 | 0.04 |
| Sodium oxalate | 0.14 | 0.14 | 0.14 |
| Hydrogen peroxide | 0.314 | 0.306 | 0.335 |
| Lactic acid | 3 | 3 | 3 |
| 10M NaOH | To pH 3.5 | To pH 3.5 | To pH 3.5 |
| Water to | 100 | 100 | 100 |
| Air | To 5.5 atm | To 5.5 atm | |
| Propane/butane 50/50 | | | 8 |
| Remaining after 2 month at 25 C. (%) | 0.303 | 0.306 | 0.285 |

A decrease in hydrogen peroxide content was very low or not present for batches propelled by air. When butane/propane was used as propellant the stability of hydrogen peroxide was significantly lower, i.e. the hydrogen peroxide content decreased significantly.

Example 4 Stability of BPO

TABLE 4

Stability of BPO in the invented composition in a pressurized container.

| Components | g/100 g product |
|---|---|
| EDTA | 0.05 |
| Lactic acid (90%) | 3.00 |
| Glycerol monolaurate | 2.5 |
| Glycerol monomyristate | 7.5 |
| Benzoyl peroxide | 5.0 |
| 10M NaOH | 3.00 |
| HPLC water | To 100 |
| Propellant, air to 5.5 atm | About 0.25 |
| pH | 4.2 |
| Stability* | |
| Initial | 50 |
| 25° C. 3 months | 48 |
| 2-8° C. 3 months | 50.1 |

*Remaining amount of BPO (mg/g)

Manufacture: EDTA, was dissolved in part of the water. Lactic acid and sodium hydroxide were added and pH adjusted. The monoglycerides were added and the mixture was heated to 70 to 75 C and kept there for 15 minutes while stirring. After 15 minutes slow cooling, less than 5 C per minute, was applied to about 35 C when crystallisation occurred followed by an increase in temperature. After the crystallisation was completed a suspension of BPO in water was added. The products were packed in spray containers consisting of a metal can and a aluminium/polymer laminate internal bag. The product was premixed with air and filled inside the bag on valve and additional air up to a pressure of 5.5 atm. The product was stored at 25° C. and 3 to 8° C. Analysis of the content of BPO was made by a HPLC-UV method. At 25° C. the product showed no degradation after 1 month storage.

The propellant (blowing agent) amount noted in table 4 refers to the amount of propellant in contact with the composition. The product demonstrated a slight degradation at 25° C. but is stable at 2 to 8° C.

Example 5

Melting point of foam was determined.

The formulations according to table 5 were manufactured according to Example 1.

TABLE 5

| | Formulations for melting point test. | | |
|---|---|---|---|
| Ingredients | G | H | I |
| 1-Glycerylmonomyristate | 6 | 9 | |
| 1-Glycerylmonolaurate | 3 | | 9 |
| Lactic acid | 3.6 | 3.6 | 3.6 |
| Hydrogen peroxide | 0.27 | 0.27 | 0.27 |
| Sodium hydroxide | 0.9 | 0.9 | 0.9 |
| Water | 77.23 | 77.23 | 77.23 |
| Melting point (° C.) | 34 | 41 | 39 |

Method and results: The melting of the formulations was tested by differential scanning calorimetry, DSC. A DSC 7 was used and about 5 mg of each formulation was weighed and put in aluminium containers. The melting peak of the preparations were determined by first cooling to about 0 C and then heating to 50 C at a rate of 5 C per minute.

The results show that a combination of the two monoglycerides makes the composition to melt when heated to body temperature and provide even application of the active to the affected tissue in the body cavity.

Example 6 Manufacture of the Formulation and Content of Lipids

TABLE 6

| Compositions (g) | | |
| --- | --- | --- |
| Invented composition | 1A | 1B |
| EDTA | 0.050 | 0.050 |
| Sodium pyrophosphate | 0.025 | 0.025 |
| Sodium stannate | 0.040 | 0.040 |
| Sodium oxalate | 0.14 | 0.14 |
| Lactic acid | 3.00 | 3.00 |
| Glycerol monolaurate | 0.2 | 7 |
| Glycerol monomyristate | 0.4 | 21 |
| NaOH | 0.70 | 0.70 |
| Hydrogen peroxide 30 w % | 1.00 | 1.00 |
| Propellant | 10 | 10 |
| HPLC water | 94.445 | 67.045 |

The formulations were manufactured by heating of water to 75 C, dissolving the salts and lactic acid in said water, the first 5 items on the ingredient list, and addition of the monoglycerides. After 15 minutes at 75 C the monoglycerides are melted and the mixture is cooled slowly to about 30 C to obtain crystallization and the cooling is stopped. After crystallization, visible as an increase in reflection of light from the composition, cooling to ambient temperature, <25 C, was undertaken. The pH was adjusted with sodium hydroxide and hydrogen peroxide was added. The manufactured compositions were packed in bulk containers.

Example 7

Products, suspensions of crystalline lipids in water manufactured according to Example 1 and with composition according to table 5 were packed under pressure in two types of pressure containers, bag on valve which is a dual compartment packaging and a single compartment packaging device. Packing in bag on valve, BOV, pressure packs were made by using a manual filling equipment. At first the composition was filled, then gas was filled outside the bag on valve and finally the gas inside the bag on valve (in contact with the composition). The gas used in contact with the composition was compressed air as well as the gas outside the bag.

TABLE 7

| Composition, one compartment pressure container. | | |
| --- | --- | --- |
|  | Type | Amount |
| Product see example 1 | Formulation 1D | 10 g |
| Gas (propellant) | Air to 5.5 atm | About 0.1 g |

TABLE 8

| Composition, bag on valve. | | |
| --- | --- | --- |
|  | Type | Amount |
| Product see example 1 | Formulation 1D | 10 g |
| Gas (propellant) in bag | Air to 5.5 atm | About 0.1 g |

TABLE 8-continued

| Composition, bag on valve. | | |
| --- | --- | --- |
|  | Type | Amount |
| Gas (propellant) in pressure container | Air to 5.5 atm | About 0.1 g |

From aerosol packing point of view both types of packages are possible to use since a solid white foam that melt at about 35° C. was generated.

Example 8, Foam Stability

Two foam products, one commercial and one according to the invention, are manufactured and pressure packed, and the foam stability is tested by a modification of an EP method for testing foam stability.

TABLE 9

| Composition of invented foam (g). | |
| --- | --- |
| Presented Invention | |
| EDTA | 0.050 |
| Sodium pyrophosphate | 0.025 |
| Sodium stannate | 0.040 |
| Sodium oxalate | 0.14 |
| Lactic acid | 3.00 |
| Glycerol monolaurate | 2.50 |
| Glycerol monomyristate | 7.50 |
| NaOH | 0.70 |
| Hydrogen peroxide 30 w % | 1.00 |
| HPLC water | 85.045 |
| Air inside bag | 0.2 |
| Air outside bag (in pressure container) | To 5.5 bar |

TABLE 10

| Commercial foam. | |
| --- | --- |
| Composition from U.S. Pat. No. 7,749,448 | |
| Dehydrated Alcohol (Ethanol), USP | 58.98 |
| Cetyl Alcohol, NP | 1.16 |
| Stearyl Alcohol, NP | 0.53 |
| Polysorbate 60, NP | 0.42 |
| Propylene Glycol, USP | 2.11 |
| Purifed Water, USP | 36.69 |
| Potassium Hydroxide, USP, 10% W/W soln. | 0.11 |
| Air inside bag | 5.5 atm |
| Air outside bag (in pressure container) | 5.5 atm |

Foam stability and adhesion test.

A glass tube, volume 60 ml, with a diameter of 26 mm was heated to 37° C. in a waterbath. The glass tube was removed and was turned upside down. The foams were administered into the tube through a foam guiding conduit, see drawing, until it was full by a controlled procedure comprising initially filling the cavity volume furthest away from the opening and then withdrawing the conduit to optimize foam delivery The tube was then returned to the water bath. The spreadability, melting and adhesion to the tube surface was studied.

Results:

The invented foam filled the volume of glass tube completely and rapidly. After about 30 seconds in the water bath it started to melt and adhered to the surface. The entire internal surface of the glass tube was covered with the melted foam as observed by the naked eye. The prior art foam collapsed at contact with the surface and did not fill the volume and only a part of the inner surface of the tube was covered with the prior art foam.

Example 9. Testing of Melting Temperatures for Mixed Monoglycerides Crystals

Monoglyceride Mixtures

Manufacture: Water was heated to 75° C. and lactic acid and then the monoglycerides were added. After 15 minutes of stirring and after melting was complete, slow cooling was applied. Cooling was stopped at 30 C when crystallization started. After crystallization, the preparation was allowed to cool to ambient temperature by passive cooling. The melting temperature of the manufactured compositions was determined by differential scanning calorimetry, DSC-7 Perkin Elmer. Melting points were tested in DSC by weighing 5 mg into aluminum containers which were closed and the temperature was run from 0 c to 45° C. at a rate of 5° C. per minute. Melting points were estimated as onset of energy uptake. The results are shown in Table 11

TABLE 11

Melting point and compositions of formulations studied.

| Ingredients | A | B | C | D | E | F | G | H | I | J | K | L |
| --- | --- | --- | --- | --- | --- | --- | --- | --- | --- | --- | --- | --- |
| Water, purified | 36.5 | 36.5 | 36.5 | 36.5 | 36.5 | 36.5 | 36.5 | 36.5 | 36.5 | 36.5 | 36.5 | 36.5 |
| Lactic acid (90%) | 1.5 | 1.5 | 1.5 | 1.5 | 1.5 | 1.5 | 1.5 | 1.5 | 1.5 | 1.5 | 1.5 | 1.5 |
| Glycerol-1-caprylate | 3 | 9 | 3 | 9 | 3 | 9 | | | | | | |
| Glyceryl-1-laurate | 9 | 3 | | | | | 3 | 9 | 3 | 9 | | |
| Glyceryl-1-myristate | | | 9 | 3 | | | 9 | 3 | | | 3 | 9 |
| Glyceryl-1-stearate | | | | | 9 | 3 | | | 9 | 3 | 9 | 3 |
| Total (g) | 50 | 50 | 50 | 50 | 50 | 50 | 50 | 50 | 50 | 50 | 50 | 50 |
| M.P. (° C.) | — | 4.4* | 39.4* | — | — | 5* | 35.5 | 34.9 | — | 34.3* | — | 43.1 |

*Separation

The melting point, onset of melting, of the monoglycerides demonstrates melting at skin temperatures for combinations of monolaurin and monomyristin, D and E. The data also demonstrates that mixtures of monoglycerides having a difference in carbon chain length of more than 2 are not forming joint crystals. Mixtures with monocaprylate as major component melt at 4 to 5° C., which is too low, while a combination of monomyristine and monostearate, G, melt at too high a temperature.

Example 10, Formulations Intended for Local Treatment of Vaginal Infections

TABLE 12

Example of a composition of a 3 mg/g hydrogen peroxide vaginal foam.

| Ingredients | Quantity % (w/w) |
| --- | --- |
| Hydrogen peroxide | 0.3 |
| EDTA | 0.05 |

TABLE 12-continued

Example of a composition of a 3 mg/g hydrogen peroxide vaginal foam.

| Ingredients | Quantity % (w/w) |
| --- | --- |
| Sodium pyrophosphate | 0.025 |
| Sodium stannate | 0.04 |
| Sodium oxalate | 0.14 |
| Glycerol monolaurate | 2.5 |
| Glycerol monomyristate | 7.5 |
| Lactic acid (90%) | 3.0 |
| Sodium hydroxide | 3.0 |
| Water demineralized | 83.745 |
| Total | 100.00 |
| Air to 5.5 atm | About 0.2% |

An example of a composition of a 3 mg/g hydrogen peroxide vaginal foam in amounts retaining the properties of the composition and the foam disclosed herein was tested, to enhance properties in contact with tissue and skin in amounts retaining the properties of the composition and the foam disclosed herein, to enhance properties in contact with tissue and skin.

The active, HP, is active against most microorganisms. Only when the microorganism can degrade HP, e.g. by catalases or similar enzymes, the antimicrobial capacity is compromised. Since the present formulation avoids this catalase effect, the formulation can be used broadly. Sexually transmitted infections, STI, such as gonorrhoea and *candida* as well as bacterial vaginosis and *trichomonas* can be possible to treat successfully with the present invention. Other infections located in the vagina, urethra, anal, oral and nasal region as well as in the ear caused by bacteria sensitive to hydrogen peroxide should be treatable with the present invention.

Body cavity includes not only as natural cavities in contact with the surroundings such as vagina, the mouth and throat, the nasal region, the ear, urethra and rectum but also artificial body cavities such as cavities formed during surgical interventions, dialysis, introduction of prostheses or wounds etc.

Vaginal or Other Body Cavity Use of the Formulation.

The present formulation can be adapted for use in body cavities for the treatment of infections caused by anaerobic bacteria. Examples of suitable body cavities are the vagina, the urinary tube, the anal and the oral cavity. Also infections in the nose and in ears may be treated with this formulation.

Examples of Infections that can be Treated with HP.

However, the cavity should be able to access from the outside without causing trauma which excludes cavities in the brain heart and the spine as well as the upper gastrointestinal channel.

A formulation useful for the treatment of vaginal infections is presented in table 8. The formulation is useful for the treatment of infections caused by microorganisms that are sensitive to hydrogen peroxide. Non limiting examples of such bacteria are associated with bacterial vaginosis, fungal infections, gonorrhoea, syphilis and chlamydia. It is also locally effective against virus.

Example 11. Formulation of Steroids in Foam

This type of foam is useful for the treatment of inflammatory diseases such as psoriasis, dermatitis and other types of eczema.

TABLE 13 formulation for the treatment of eczema.

| Ingredient | g/100 g |
| --- | --- |
| 1-Glycerylmonolaurate | 5 |
| 1-Glycerylmonomyristate | 15 |
| Mometasone furanoate | 0.1 |
| Glycerol | 3 |
| Water | 76.9 |
| Air to 5.5 atm | 0.25 |

Manufacture was performed by heating the monoglycerides with water to 75 C and stirring for 15 minutes, followed by addition of glycerol and mometasone furanoate and then slow cooling to crystalisation at about 35 C. The product was then cooled to ambient temperature. Testing of foaming capacity and foam quality was made by whipping air into the bulk cream at ambient pressure. A method for this has been developed and after 30 seconds a foam was formed. The foam was stable for more than 30 days in normal atmosphere at 25 C as evaluated by microscope. The entrapped airbubbles suggested that the structure was made up by planar crystals and not by a liquid bilayer film.

Example 12, Foam for Treatment of Urinary Incontinence

TABLE 14 formulation for the treatment of urinary incontinence.

| Ingredient | g/100 g |
| --- | --- |
| 1-Glycerylmonolaurate | 5 |
| 1-Glycerylmonomyristate | 15 |
| Oxybutynine chloride | 0.1 |
| Lactic acid | 1 |
| Glycerol | 3 |
| Water | 75.9 |
| Air (milligram) | 60 |

Manufacture was performed by heating the monoglycerides with water to 75 C and stirring for 15 minutes, followed by addition of glycerol and Oxybutynine chloride and then slow cooling to crystalisation at about 35 C. The product was then cooled to ambient temperature. Testing of foaming capacity and foam quality was made by whipping air into the bulk cream at ambient pressure. A method for this has been developed and after 30 seconds a foam was formed. The foam was stable for more than 30 days in normal atmosphere at 25 C as evaluated by microscope. The entrapped airbubbles suggested that the structure was made up by planar crystals and not by a liquid bilayer film.

Example 13, Foam for Treatment of Psoriasis

TABLE 15 formulation for the treatment of psoriasis.

| Ingredient | g/100 g |
| --- | --- |
| 1-Glycerylmonolaurate | 5 |
| 1-Glycerylmonomyristate | 15 |
| Calcipotriol | 0.005 |
| Glycerol | 3 |
| Water to | 100 |
| Air (milligram) | 110 |

Manufacture was performed by heating the monoglycerides with water to 75 C and stirring for 15 minutes, followed by slow cooling to crystalisation at about 35 C. The product was then cooled to ambient temperature. Calcipotriol and glycerol was added after crystallization. Testing of foaming capacity and foam quality was made by whipping air into the bulk cream at ambient pressure. A method for this has been developed and after 30 seconds a foam was formed. The was stable for more than 30 days in normal atmosphere at 25 C as evaluated by microscope. The entrapped airbubbles suggested that the structure was made up by planar crystals and not by a liquid bilayer film.

Example 14, Foam for Treatment of Itch

TABLE 16 formulation for the treatment of itch.

| Ingredient | g/100 g |
| --- | --- |
| 1-Glycerylmonolaurate | 5 |
| 1-Glycerylmonomyristate | 15 |
| Doxepin | 5 |
| Glycerol | 3 |
| Water | 72 |
| Air (milligram) | 37 |

Manufacture was performed by heating the monoglycerides with water to 75 C and stirring for 15 minutes, followed by addition of glycerol and Doxepine and then slow cooling to crystalisation at about 35 C. The product was then cooled to ambient temperature. Testing of foaming capacity and foam quality was made by whipping air into the bulk cream at ambient pressure. A method for this has been developed and after 30 seconds a foam was formed. The foam was stable for more than 30 days in normal atmosphere at 25 C as evaluated by microscope. The entrapped airbubbles suggested that the structure was made up by planar crystals and not by a liquid bilayer film. FIG. 1 is a picture of the foam and FIG. 2 is a picture of the foam after one month.

Example 15 Foam for Treatment of Local Inflammation

TABLE 17 formulation for the treatment of local inflammation.

| Ingredient | g/100 g |
|---|---|
| 1-Glycerylmonolaurate | 5 |
| 1-Glycerylmonomyristate | 15 |
| Diclofenac diethylamine | 1.16 |
| Propyleneglycol | 5 |
| Water to100 | 100 |
| Air (milligram) | 37 |

Manufacture was performed by heating the monoglycerides with water to 75 C and stirring for 15 minutes, followed by addition of glycerol and Diclofenac diethylamine and then slow cooling to crystalisation at about 35 C. The product was then cooled to ambient temperature. Testing of foaming capacity and foam quality was made by whipping air into the bulk cream at ambient pressure. A method for this has been developed and after 30 seconds a foam was formed. The foam was stable for more than 30 days in normal atmosphere at 25 C as evaluated by microscope. The entrapped airbubbles suggested that the structure was made up by planar crystals and not by a liquid bilayer film.

Example 16 Foam for Treatment of Fungal Infections

TABLE 18 antifungal formulation

| Ingredient | g/100 g |
|---|---|
| 1-Glycerylmonolaurate | 5 |
| 1-Glycerylmonomyristate | 15 |
| Terbinafine HCl | 1 |
| Propyleneglycol | 7 |
| Urea | 1 |
| Lactic acid | 2 |
| Water to100 | 100 |
| Air (milligram) | 12 |

Manufacture was performed by heating the monoglycerides with water to 75 C and stirring for 15 minutes, followed by addition of glycerol and Terbinafine HCl stirring for another 5 minutes and then slow cooling to crystalisation at about 35 C. The product was then cooled to ambient temperature. Testing of foaming capacity and foam quality was made by whipping air into the bulk cream at ambient pressure. A method for this has been developed and after 30 seconds a foam was formed. The foam was stable for more than 30 days in normal atmosphere at 25 C as evaluated by microscope. The entrapped airbubbles suggested that the structure was made up by planar crystals and not by a liquid bilayer film.

Example 17 Foam for Dry and Irritated Skin and Body Cavities

TABLE 19

Formulation for dry skin

| Ingredient | g/100 g |
|---|---|
| 1-Glycerylmonolaurate | 5 |
| 1-Glycerylmonomyristate | 15 |
| Lactic acid | 2 |
| Glycerol | 5 |
| Myrj 59 | 0.1 |
| Water to | 100 |
| Air (milligram) | 60 |

Manufacture was performed by heating the monoglycerides with water to 75 C and stirring for 15 minutes, followed by addition of Lactic acid, glycerol and Myrj 59, and then slow cooling to crystalisation at about 35 C. The product was then cooled to ambient temperature. Testing of foaming capacity and foam quality was made by whipping air into the bulk cream at ambient pressure. A method for this has been developed and after 30 seconds a foam was formed. The foam was stable for more than 30 days in normal atmosphere at 25 C as evaluated by microscope. The entrapped airbubbles suggested that the structure was made up by planar crystals and not by a liquid bilayer film.

It was unexpected and surprising that the foam formed by whipping the blowing agent (such as air) into the suspension exhibited long term stability. It was also unexpected and surprising that the foam formed by allowing the blowing agent to expand and form the foam also exhibited long term stability.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A foam-forming pharmaceutical composition for delivering active agents to a surface of the body or to body cavities comprising:
water;
solid lipid crystals suspended in the water, the solid lipid crystals having a melting point in their crystalline state of less than 37° C. and more than 25° C.; and
a nonlipophillic propellant for blowing the composition and forming a foam, wherein the propellant comprises at least one selected from the group consisting of air, combinations of oxygen and nitrogen, and combinations of oxygen, nitrogen and carbon dioxide,
wherein the solid lipid crystals being present in an amount to support a foam blown by the propellant, the composition is configured for application to the body cavity in blown form, and the composition is configured to degrade in the body cavity at the melting point and release contents of the foam to tissues in the body cavity, wherein the propellant is from 0.0001 to 0.5% by weight of the composition, wherein the lipid crystals are selected from the group consisting of phospholipids, mono or di acylglycerides, lipid esters of lactic acid, and n-acetylethanolamides.

2. The foam-forming composition according to claim 1, wherein the lipid crystals being present in an amount of at least 0.5% and at the most 28% by weight based on the weight of composition.

3. The foam-forming composition according to claim 1, comprising an effective amount of a medically active, cosmetic or relieving agent.

4. The foam-forming composition according to claim 1, wherein the propellant in contact with the composition is hydrophilic.

5. A packaged foam-forming composition comprising:
the composition according to claim 1, wherein
the composition is contained in a single or dual compartment container.

6. The foam-forming composition according to claim 1, wherein the composition is under a pressure of 10 atm down to atmospheric pressure by the propellant.

7. The packaged foam-forming composition according to claim 5, wherein the container comprises a foam guiding conduit adapted to provide vaginal delivery of the foam.

8. The foam-forming composition according to claim 1, wherein the lipid crystals comprise at least one selected from the group consisting of monoacylglycerides having a carbon chain length of 10 to 16 carbons and where the relation between the monoacylglycerides are 1:20 to 20:1.

9. The foam-forming composition according to claim 3, wherein the active agent comprises hydrogen peroxide for the treatment of infections in the body cavities.

10. The foam-forming composition according to the claim 3, wherein the active agent comprises anticholinergic or bladder relaxing compounds suitable for treatment of urinary incontinence.

11. The foam-forming composition according to the claim 3, wherein the active agent comprises anti-psoriatic drugs suitable for treatment of psoriasis.

12. The foam-forming composition according to the claim 3, wherein the active agent comprises compounds suitable for treatment of acne.

13. The foam-forming composition according to the claim 3, wherein the active agent comprises antiinflammary agents suitable for treatment of local infalmmations.

14. A foam-forming composition adapted for treating a disease on or in skin or in a body cavity comprising:
an active ingredient;
an effective amount of hydrogen peroxide;
monoglyceride crystals in an amount to form a foam;
at least one acid and/or buffer which is present in an amount to provide a pH of 3 to 5 within the body cavity or on the skin;
a nonlipophillic propellant in an amount to blow the foam-forming composition and form a foam, and the nonlipophillic propellant cannot dissolve the crystal structure of the monoglycerides at storage temperatures between 0 and 30° C., wherein the propellant comprises at least one selected from the group consisting of air, combinations of oxygen and nitrogen, and combinations of oxygen, nitrogen and carbon dioxide; and
water, wherein the foam-forming composition is configured for application to the body cavity and blown to form the foam and the foam is configured to degrade at a body temperature to release the active ingredient to skin or to tissues in the body cavity at a pH of 3 to 5, wherein the nonlipophillic propellant is from 0.0001 to 0.5% by weight of the composition.

15. The foam-forming composition according to claim 14, wherein the monoglyceride crystals comprise at least two monoglycerides having an average chain length of 12 and 14.

16. The foam-forming composition according to claim 14, wherein the foam-forming composition is formulated to provide the foam having a melting point below 37° C.

17. The foam-forming composition according to claim 14, wherein the buffer is lactic acid and Sodium Hydroxide.

18. The foam-forming composition according to claim 14, wherein the foam-forming composition is storage stable.

19. The foam-forming composition according to claim 14, wherein the foam-forming composition is pressurized by the propellant.

20. The foam-forming composition according to claim 14, wherein the foam-forming composition is packaged together with instructions for use for the treatment of skin, wound, vaginal, oral, anal, urethral, nasal and ear infections.

21. The foam-forming composition according to claim 20, wherein the instructions for use comprise use for local treatment of sexually transmitted diseases.

22. The foam-forming composition according to claim 14, wherein the foam-forming composition is packaged together with instructions for use for local treatment of sexually transmitted diseases.

23. The foam-forming composition according to claim 14, wherein the foam-forming composition contains at least one stabilizer for hydrogen peroxide.

24. The foam-forming composition according to claim 14, wherein the foam-forming composition is under a pressure of 10 atm down to atmospheric pressure by the propellant.

25. The foam-forming composition according to claim 1, wherein the propellant is from 0.0001 to 0.25% by weight of the composition.

26. The foam-forming composition according to claim 14, wherein the nonlipophillic propellant is from 0.0001 to 0.25% by weight of the composition.

27. The foam-forming composition according to claim 1, wherein the propellant is from 0.0001 to 0.1% by weight of the composition.

28. The foam-forming composition according to claim 14, wherein the nonlipophillic propellant is from 0.0001 to 0.1% by weight of the composition.

* * * * *